United States Patent
Radtke

(10) Patent No.: US 11,980,630 B2
(45) Date of Patent: May 14, 2024

(54) **FLEX-NUCLEOSIDE ANALOGUES, NOVEL THERAPEUTICS AGAINST FILOVIRUSES AND FLA

Figure 2D

Plates Statistics Chart

| Index | Cell line | Pathogen | MOI | Plate ID | Well Masking | Nuclei No- NC | %infection NC | Z factor | No of Fields | E86a4, EC50 nm | E864 SD |
|---|---|---|---|---|---|---|---|---|---|---|---|
| 1 | Hela | EBOV | 1.5 | AA00004584 | 0% | 5405.5 | 42.20 | 0.66 | 5 | 77.6 | 11.4 |
| 2 | Hela | MARV | 1 | AA00004582 | 0% | 5611 | 40.35 | 0.59 | 5 | 104.0 | 9.0 |
| 3 | Hela | SUDV | 0.1 | AA00004581 | 0% | 6082 | 29.40 | 0.67 | 5 | 144.4 | 16.9 |

Dose response of Control compound E864

Figure 2 A

A EBOV /Hela

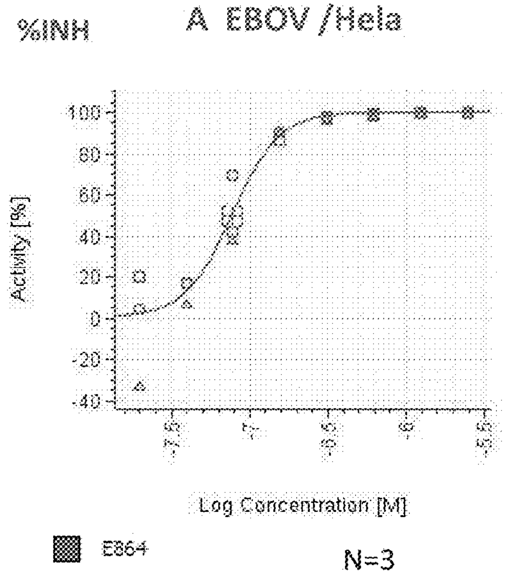

Figure 2 B

B MARV/Hela

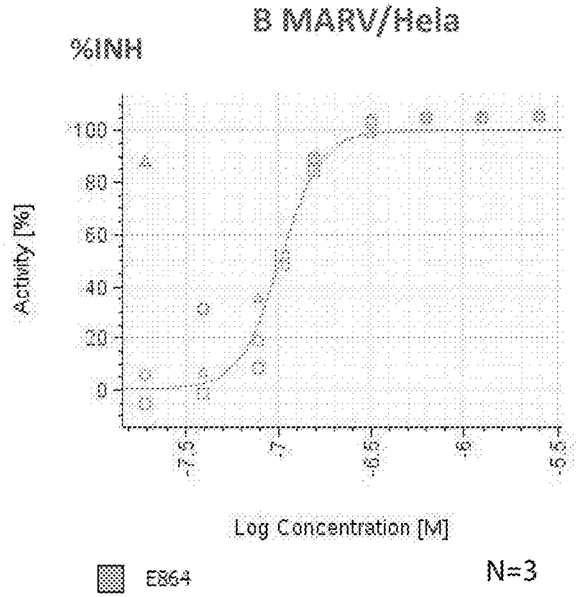

Figure 2 C

C SUDV/Hela

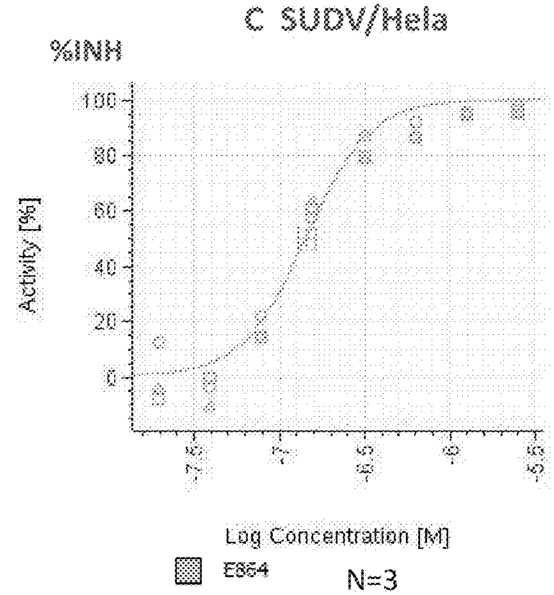

Figure 2 A, B, C and D

EBOV / Hela

Figure 3 A    %INH

Figure 3 B    %Viability

| Compound ID | Cell line | Pathogen | Plate ID | Fit Model | EC50 uM | SD | EC90 | CC50 uM | CC%/EC50 |
|---|---|---|---|---|---|---|---|---|---|
| HP105 | Hela | EBOV | AA00004584 | 2pHill (AC50,n) | 44.46 | 13.4439 | 158.81 | >100 | >2.3 |
| MR064 | Hela | EBOV | AA00004584 | 2pHill (AC50,n) | 29.10 | 8.9000 | 79.13 | 100 | 3.4 |

Figure 3C

Figures 3 A, B and C

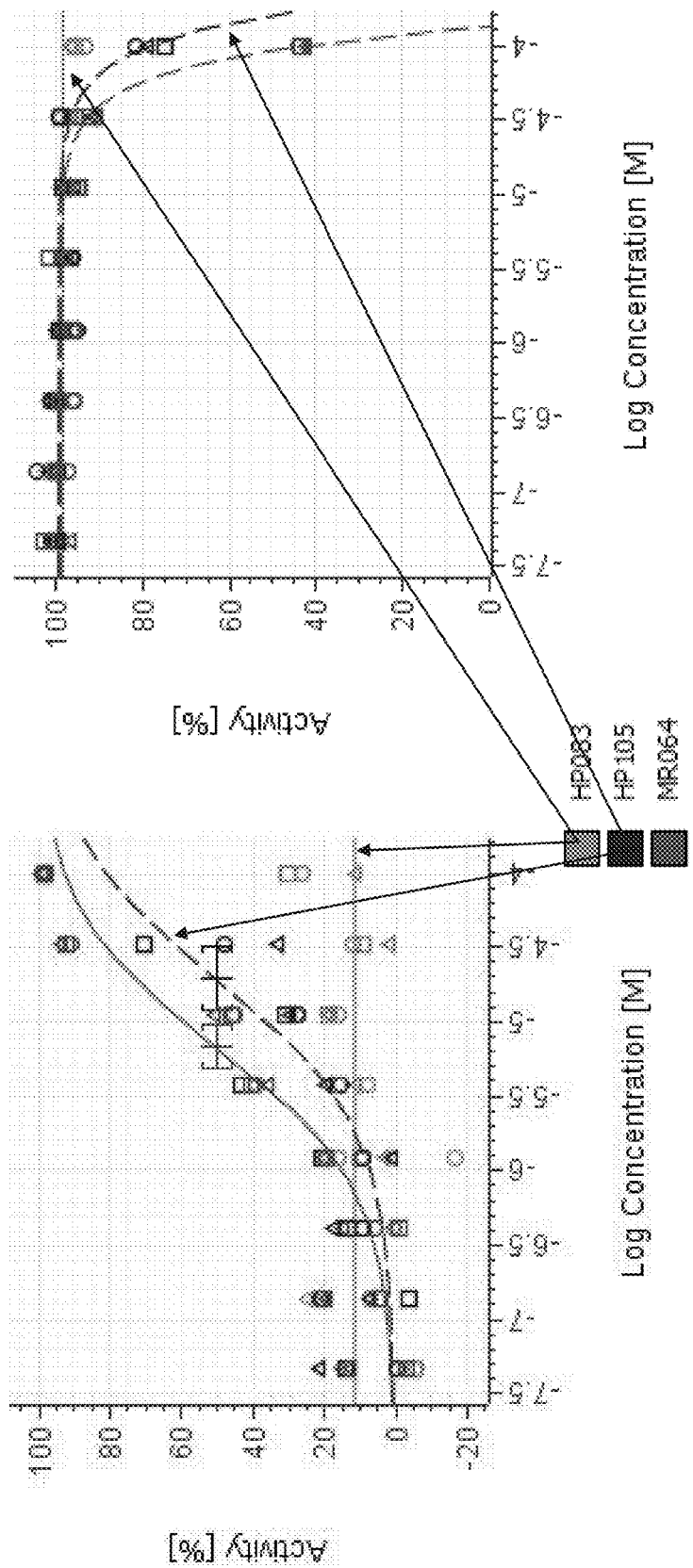
Figure 4 A, B and C

Figures 5 A, B and C

SARS - CoV 0,6 μM complex SARS (12HC/7HC8)
0,5 μM primer*/template

3'─────────── LS15
5'-CUAUCCCAUGUGAUUUUAC───── LS2*
          ───── polymerization ──▶

FLEX-NUCLEOSIDE ANALOGUES, NOVEL THERAPEUTICS AGAINST FILOVIRUSES AND FLAVIVIRUSES

CROSS-REFERENCE TO RELATED APPLICATION

This application is a divisional application of copending U.S. patent application Ser. No. 16/629,057 filed on Jan. 7, 2020, now U.S. Pat. No. 112,533,529, which was filed under the provisions of 35 U.S.C. § 371 and claims the priority of International Patent Application No. PCT/US2018/015352 filed on Jan. 26, 2018 which in turn claims priority to U.S. Provisional Patent Application No. 62/539,034 filed on Jul. 31, 2017, the contents of which is hereby incorporated by reference herein for all purposes.

STATEMENT OF FEDERALLY SPONSORED RESEARCH

This invention was made with government support under Grant Number Grant Number R21AI097685 and T32GM066706 awarded by the National Institutes of Health. The government has certain rights in the invention.

FIELD OF INVENTION

The present invention is directed to compounds, methods and compositions for treating or preventing filoviruses and/or flaviviruses using nucleosides analogues. Specifically, the present invention provides for the design and synthesis of acyclic fleximer nucleoside analogues having increased flexibility and ability to alter their conformation to provide increased antiviral activity potential with the result of inhibiting several coronaviruses.

BACKGROUND OF THE INVENTION

Viruses are small infectious agents that can only multiply within the cells of animals, plants, and bacteria. The structures of viruses are simple compared to living cells and contain a small haploid DNA or RNA genome and a protein or glycoprotein coat called a capsid. In addition, some viruses called enveloped viruses are surrounded by a lipid membrane.

A number of viruses appear on the United States National Institutes of Allergy and Infectious Disease (NIAID) list of Emerging Diseases/Pathogens list, which include Flaviviruses (Dengue, Zika and West Nile) and Filoviruses (Ebola, Sudan and Marburg) to name a few.

Filoviruses are enveloped viruses with a genome consisting of one linear single-stranded RNA segment of negative polarity. The viral genome encodes 7 proteins. Nucleoprotein (NP), virion protein 35 kDa (VP35) and virion protein 30 kDa (VP30) are associated with the viral ribonucleoprotein complex. Members of the filovirus genus include Zaire Ebola virus, Sudan Ebola virus, Reston Ebola virus, Cote d'Ivoire Ebola virus and Marburg virus. Ebola and Marburg viruses can cause severe hemorrhagic fever and have a high mortality rate. Ebola virus (Zaire and Sudan species) was first described in 1976 after outbreaks of a febrile, rapidly fatal hemorrhagic illness were reported along the Ebola River in Zaire (now the Democratic Republic of the Congo) and Sudan. The natural host for Ebola viruses is still unknown. Marburg virus, named after the German town where it was first reported in 1967, is primarily found in equatorial Africa. The host range of Marburg virus includes non-human and human primates. Marburg made its first appearance in Zimbabwe in 1975 and was later identified in other African countries, including Kenya (1980 & 1987) and Democratic Republic of the Congo (1999).

Viruses in the genus flavivirus are known to cause viral hemorrhagic fevers (VHFs). Flaviviruses are enveloped viruses with a genome consisting of one linear single-stranded RNA segment of positive pola The polyprotein is co- and post-transcriptionally cleaved by cell signal peptidase and the viral protease to generate individual viral proteins. Viral structural proteins include capsid (C), precursor to M (prM), minor envelope (M) and major envelope (E).

Members of the flavivirus genus include yellow fever virus, Apoi virus, Aroa virus, Bagaza virus, Banzi virus, Bouboui virus, Bukalasa bat virus, Cacipacore virus, Carey Island virus, Cowbone Ridge virus, Dakar bat virus, dengue virus, Edge Hill virus, Entebbe bat virus, Gadgets Gully virus, Ilheus virus, Israel turkey meningoencephalomyelitis virus, Japanese encephalitis virus, Jugra virus, Jutiapa virus, Kadam virus, Kedougou virus, Kokobera virus, Koutango virus, Kyasanur Forest disease virus, Langat virus, Louping ill virus, Meaban virus, Modoc virus, Montana myotis leukoencephalitis virus, Murray Valley encephalitis virus, Ntaya virus, Omsk hemorrhagic fever virus, Phnom Phenh bat virus, Powassan virus, Rio Bravo virus, Royal Farm virus, Saboya virus, Sal Vieja virus, San Perlita virus, Saumarez Reef virus, Sepik virus, St. Louis encephalitis virus, Tembusu virus, tick-borne encephalitis virus, Tyuleniy virus, Uganda S virus, Usutu virus, Wesselsbron virus, West Nile virus, Yaounde virus, Yokose virus, Zika virus, cell fusing agent virus and Tamana bat virus.

There are relatively few prophylactic or therapeutic agents for treatment of viral diseases caused by Flaviviruses and Filoviruses. The need for new and more effective antiviral therapeutics, particularly those targeting emerging and reemerging infectious diseases and pathogens continues to increase. Thus, in light of the above discussion, there is a need for discovering and providing new and more efficient antiviral drugs.

SUMMARY OF THE INVENTION

The present invention provides for flexible and modified nucleoside analogues that allow access to more potential binding sites with the ability to retain their potency against viral diseases caused by Flaviviruses and Filoviruses since they can "wiggle and jiggle" in the binding site. These findings are causing a paradigm shift in drug design having antiviral activity.

In one aspect, the present invention provides for a series of doubly flexible nucleoside analogues based on the acyclic nucleosides and the flex-base moiety found in the fleximers having antiviral activity against Flaviviruses and Filoviruses selected from compounds according to the following:

(HP105)

-continued (MR064)

(2MR04)

(HP083)

Wherein Ac is CH3—C(=O), or pharmaceutically acceptable salt, isomer, hydrate, prodrug or solvate thereof.

In another aspect, the present invention provides for the use of modified nucleosides of the present invention in a medicament for medicine. In a more specific embodiment hereof, said use as a medicine is for the prevention or treatment of a filovirus, flavivirus and/or coronavirus in a subject, mammal or human. Preferably, a therapeutically effective amount of the acyclic fleximer nucleoside analogue is from 0.05 to 50 mg per kilogram body weight of the subject per day.

In yet another aspect, the present invention provides for contacting a cell infected with a filovirus or flavivirus or to be infected with a filovirus or flavivirus with at least one of the modified nucleosides provided herein, wherein the amount of the modified nucleosides is from about 1 µg/ml to about 40 µg/ml, and more preferably, from about 3 µg/ml to about 20 µg/ml.

In another aspect, the present invention provides for the manufacture of a medicament comprising the modified nucleosides of the present invention for the treatment of a filovirus or flavivirus.

In a further aspect, the present invention provides for the use of the modified nucleosides of the present invention for the prevention or treatment of a filovirus and/or flavivirus, wherein the modified nucleosides comprise the compounds 1, 2, 3 or 9.

In a still further aspect, the present invention provides for a pharmaceutical composition comprising at least one of the modified nucleosides of the present invention and a pharmaceutically acceptable carrier.

In another aspect, the invention also provides novel intermediates or prodrugs which are useful for preparing the compounds of the invention or converted to active agents in vivo, respectively. Prodrugs are selected and prepared in order to improve some selected property of the molecule, such as water solubility or ability to cross a membrane, temporarily. Most common (biologically labile) functional groups utilized in prodrug design include carbonates, esters, amino acyl esters, amides, carbamates, oximes, imines, ethers or phosphates.

In yet another aspect the present invention provides for nucleoside analogues based on the acyclic nucleoside acyclovir (ACV) selected from the following compounds:

X=OMe, $NH_2$
Y=OMe, $NH_2$,H
R=H, Ac, McGuigan, MP, DP, TP
or a pharmaceutically acceptable salt, isomer, hydrate, prodrug or solvate thereof.

In a further aspect, the invention also provides a method of inhibiting a filovirus or flavivirus administering to a mammal infected with such a filovirus or flavivirus a compound selected from compounds 1, 2, 3 or 9 and pharmaceutically effective salts thereof in an amount to effectively inhibit the replication of a filovirus or flavivirus in infected cells in the mammal.

In a still further aspect, the present application provides for a method of treating a filovirus, flavivirus or coronavirus in a patient, comprising administering to said patient a therapeutically effective amount of a compound of the present invention, and at least one additional therapeutic agent having anti-viral properties.

In other aspects, methods for synthesis, analysis, separation, isolation, purification, characterization, and testing of the compounds of this invention are provided.

BRIEF DESCRIPTION OF THE FIGURES

FIG. 2A shows the dose response of Control compound E864 for treatment of EBOV,

FIG. 2B shows the dose response of Control compound E864 for treatment of MARV and FIG. 2C shows the dose response of Control compound E864 for treatment of SUDV and FIG. 2D shows plates statistics chart.

FIG. 3A shows the percentage inhibition (% INH) and FIG. 3B shows percent viability for compounds HP105 and MR064 for inhibition of EBOV in Hela cells and FIG. 3C shows a table with results.

FIG. 4A shows the percentage inhibition (% INH) and FIG. 4B shows percent viability for compounds HP083, HP105 and MR064 for inhibition of SUDV in Hela cells and FIG. 4C shows a table with results.

FIG. 5A shows the percentage inhibition (% INH) and FIG. 5B shows percent viability for compounds HP083, HP105 and MR064 for inhibition of MARV in Hela cells

Figure 7:
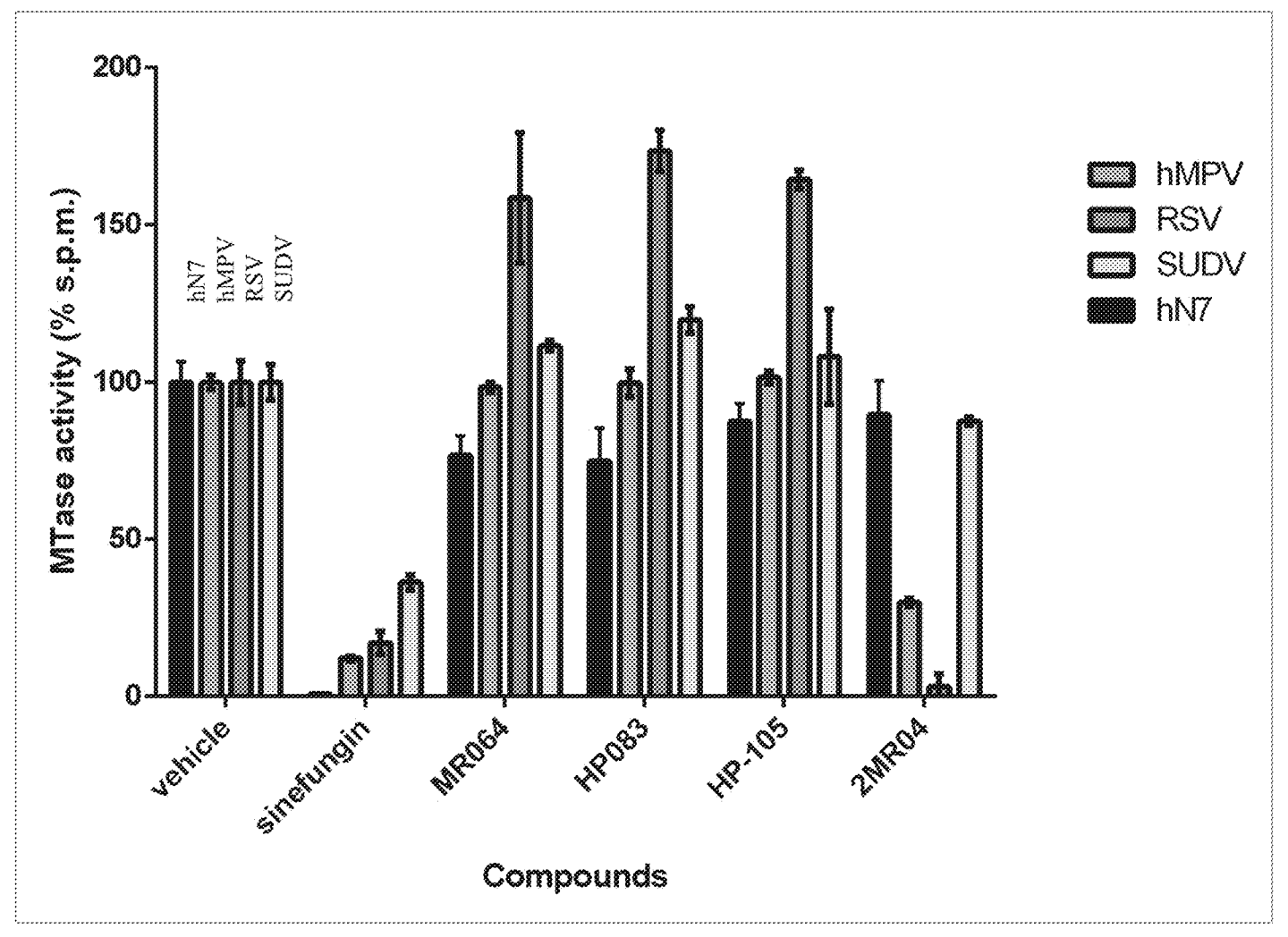

FIG. 7 shows MTase activity for multiple viruses using sinefungin as a control and comparing to compounds 2MR04, MR064, HP105 and HP083.

Figure 8:
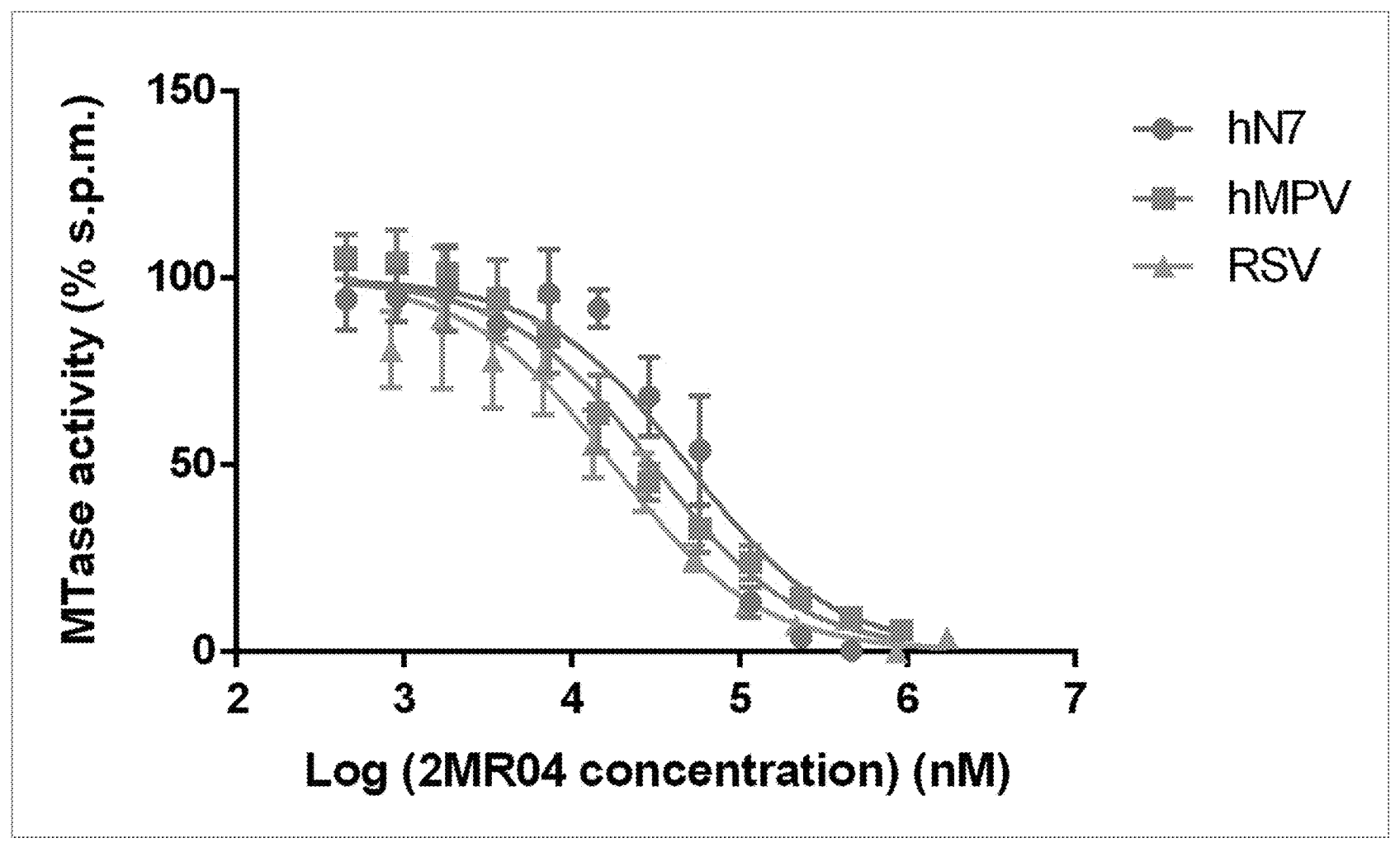

FIG. 8 shows MTase activity for multiple viruses using the 2MR04 compound.

FIG. 13 shows blots of formation of nucleotide sequences using the 2MR04 inhibitor against MERS, SEQ ID NO 1.

FIG. 14 shows blots of formation of nucleotide sequences using the 2MR04 inhibitor against SARS, SEQ ID NO. 1.

Figure 15:
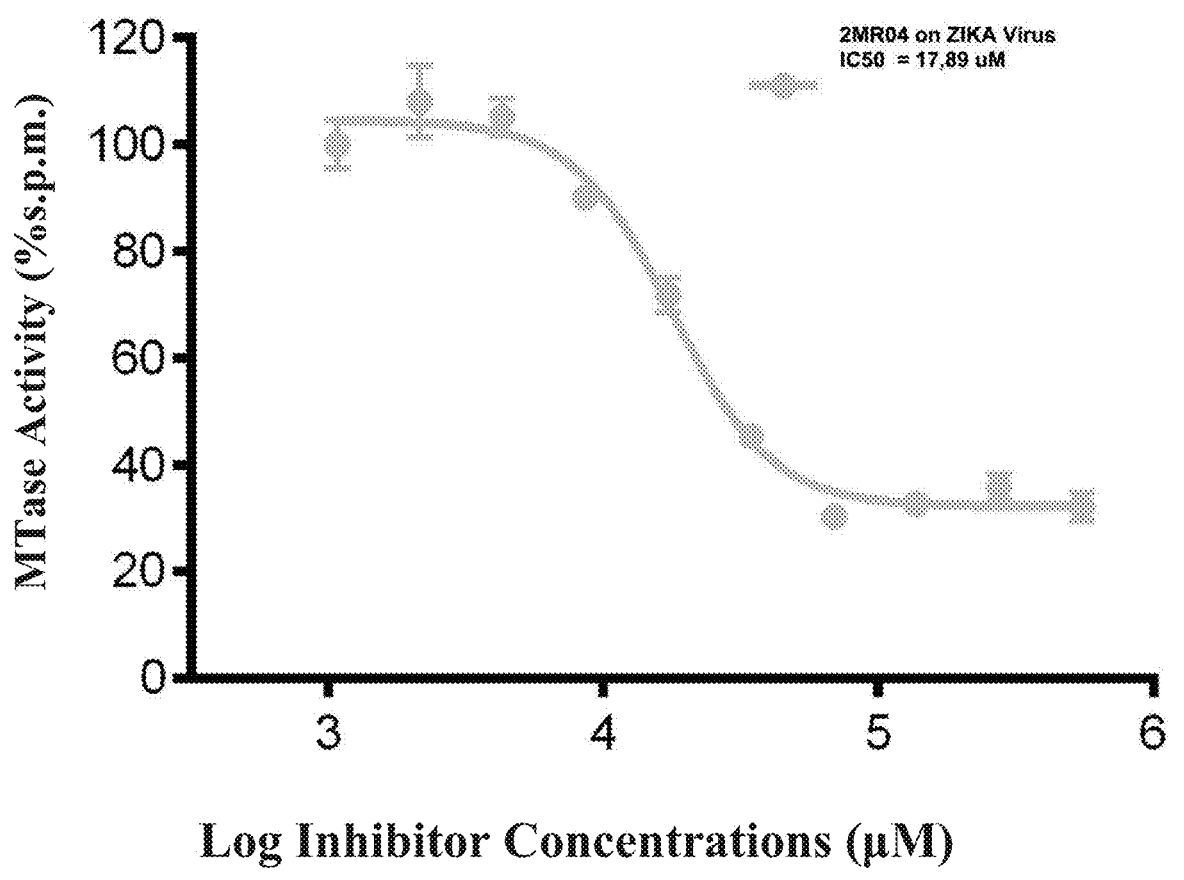

FIG. 15 shows the effect of 2MR04 on Zika Virus.

DETAILED DESCRIPTION OF THE INVENTION

Figure 1:
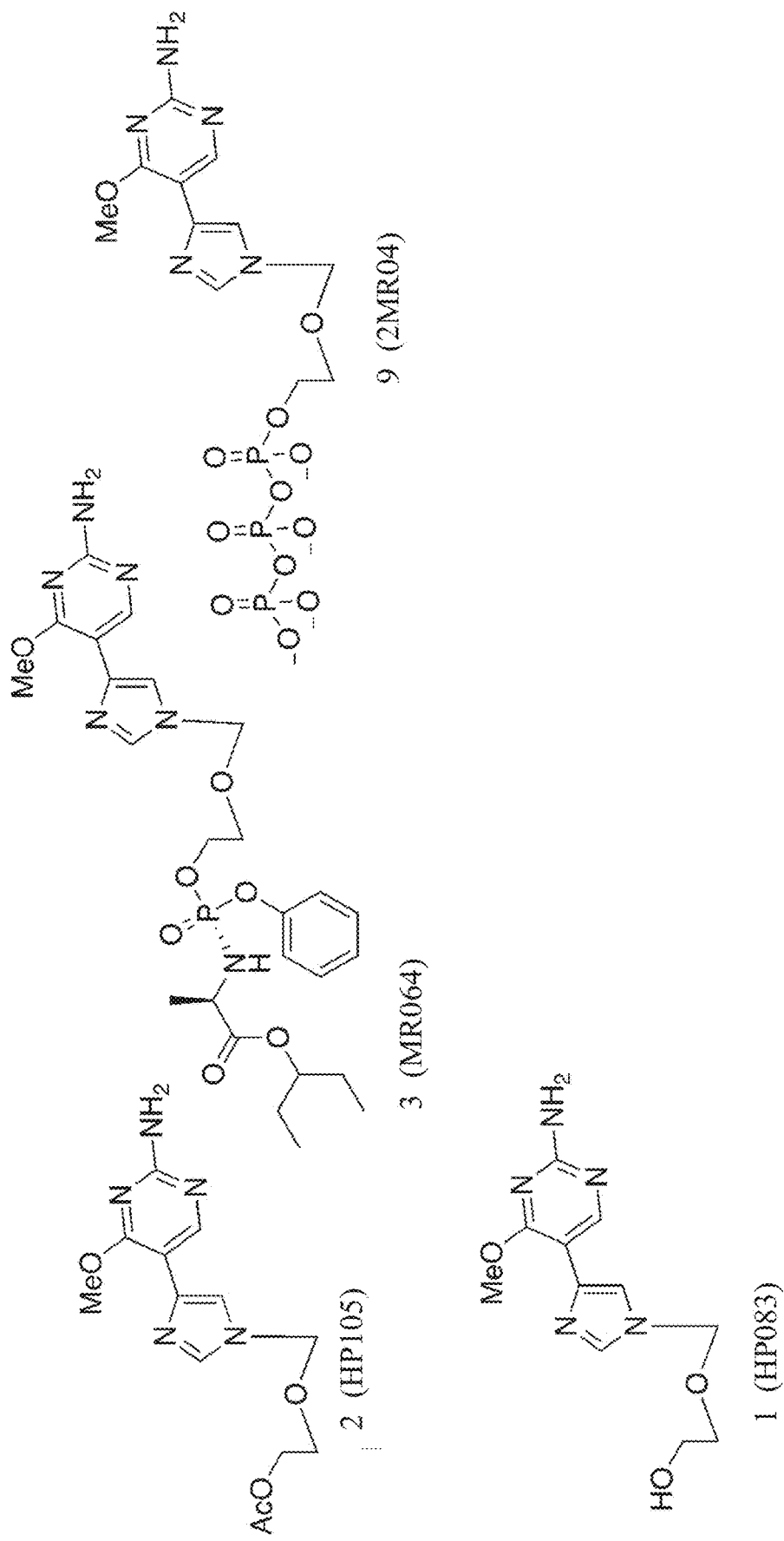
FIG. 1 shows the structures of the target flexible nucleoside analogues of the present invention.
Figures 5, 5C:
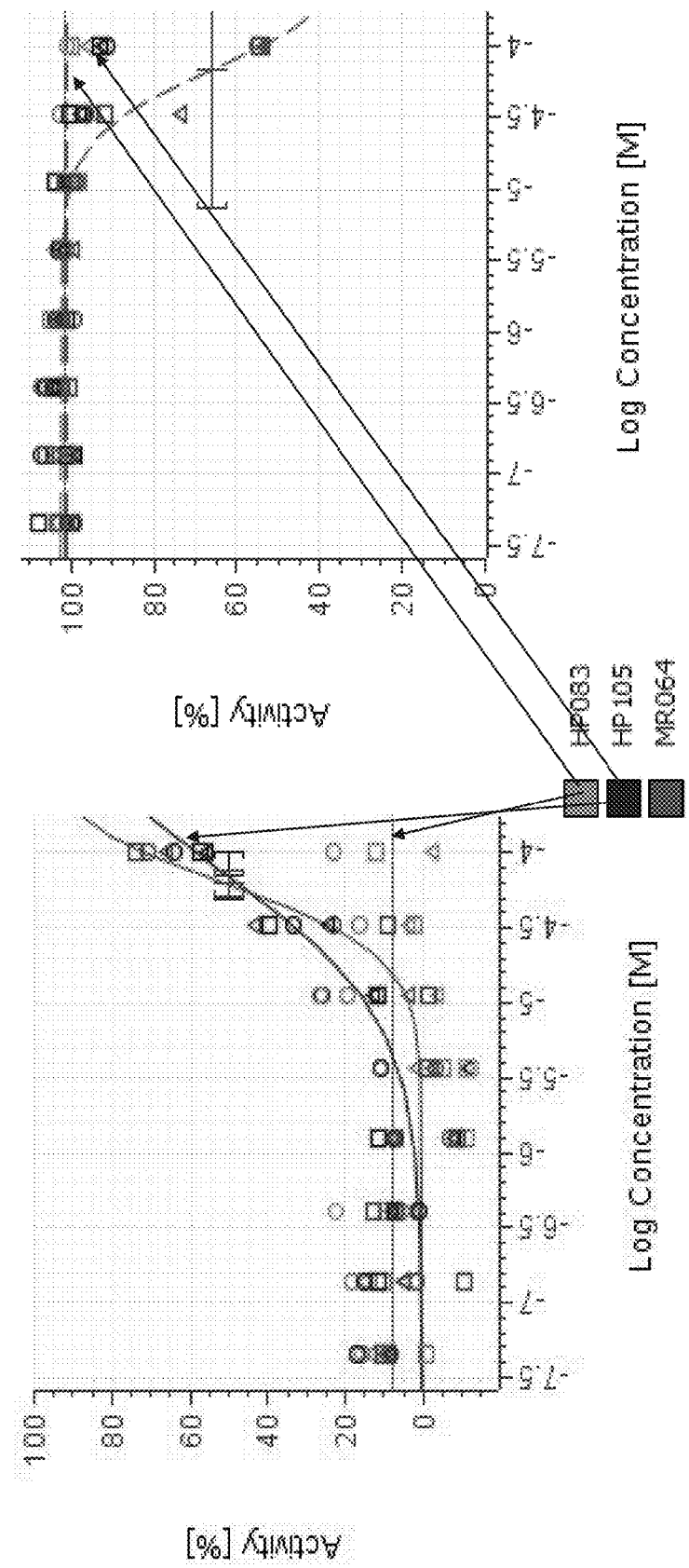
FIG. 5C shows a table with results.
Figure 6:
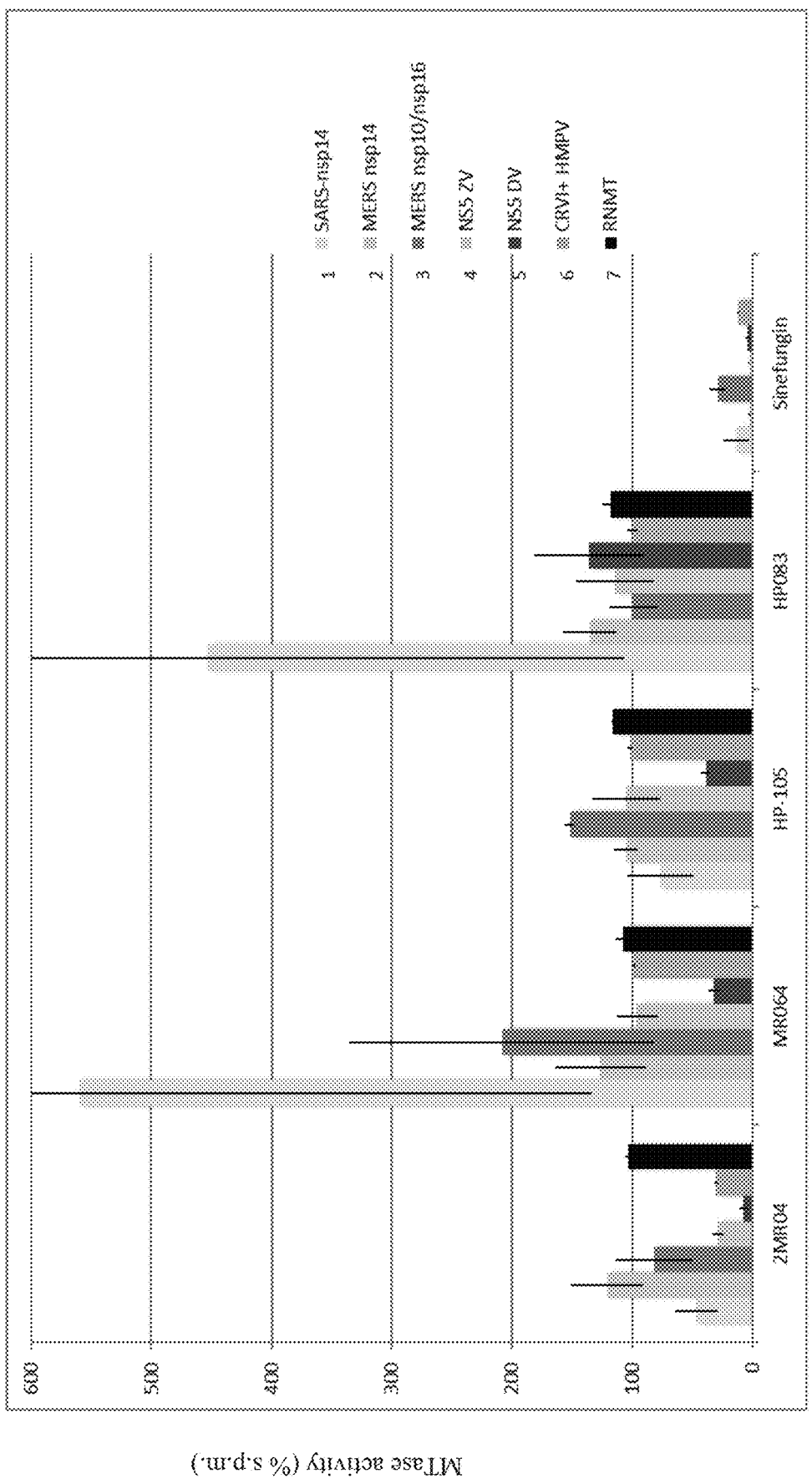
FIG. 6 shows MTase activity for multiple viruses using sinefungin as a control and comparing to compounds 2MR04, MR064, HP105 and HP083.
Figure 9:
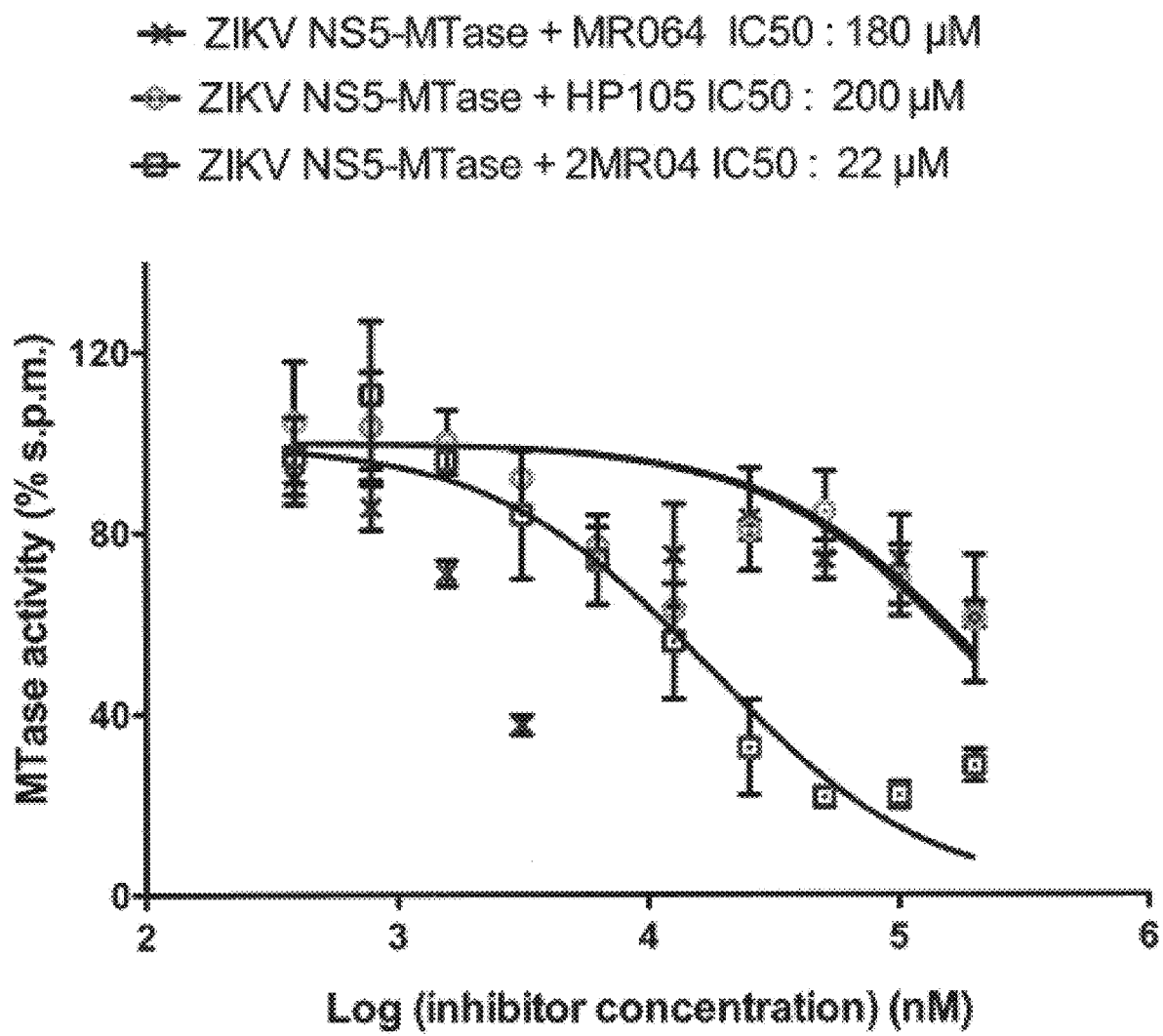
FIG. 9 shows MTase activity for ZIKA virus using compounds 2MR04, MR064 and HP105.
Figure 10:
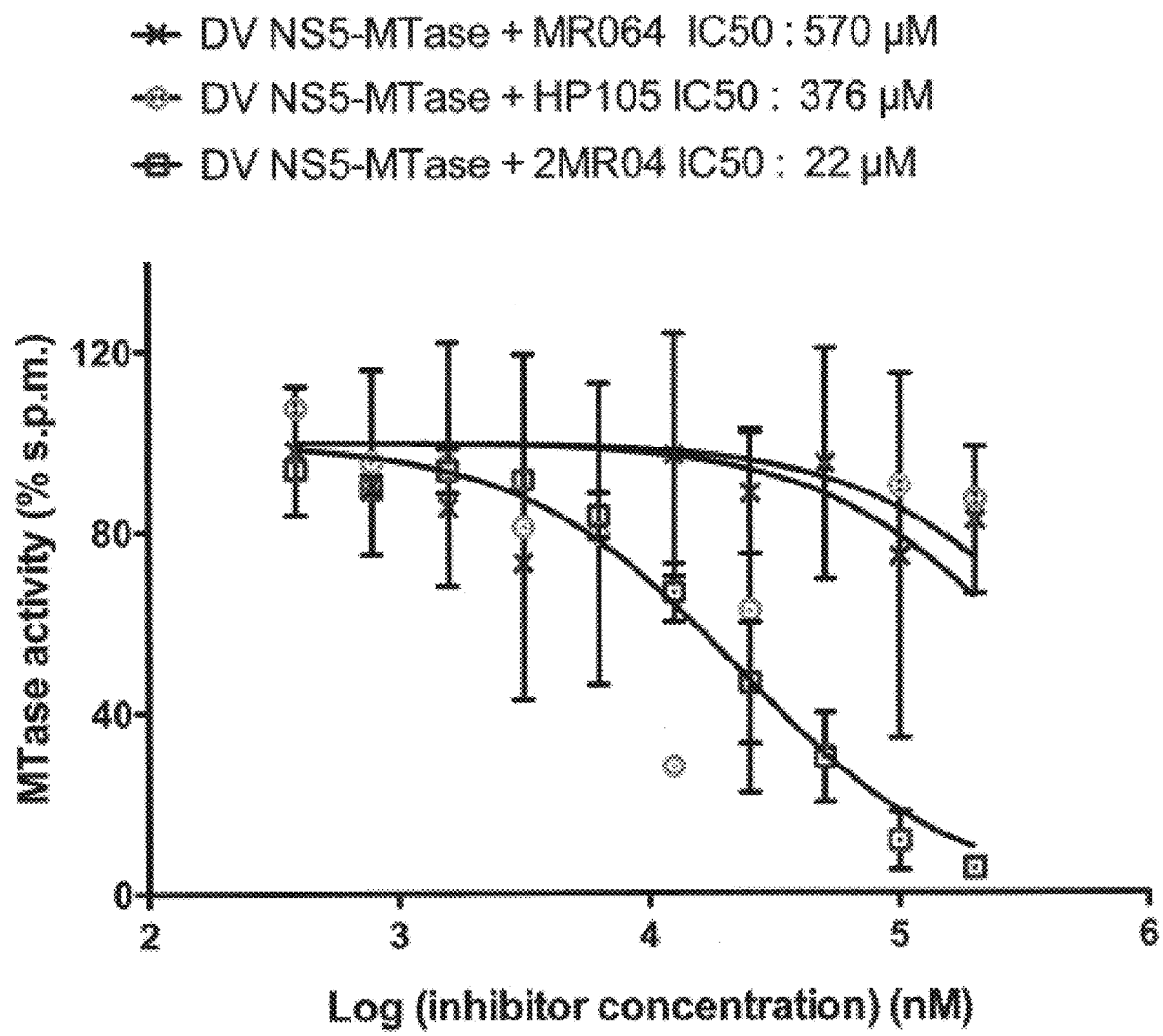
FIG. 10 shows MTase activity for Dengue virus using compounds 2MR04, MR064 and HP105.

Unique nucleoside analogues have been termed 'fleximers' and were designed to explore how nucleobase flexibility affects the recognition, binding, and activity of nucleoside(tide) analogues. The fleximers possess a purine base scaffold in which the pyrimidine moiety is attached by a single carbon-carbon bond, rather than being 'fused' as is typical for the purines. These analogues are designed to retain all of the requisite purine hydrogen bonding patterns while allowing the nucleobase to explore alternative binding modes.

The present invention provides for a series of doubly flexible nucleoside analogues based on the acyclic sugar scaffold of acyclovir and the flex-base moiety found in the fleximers. The target compounds were evaluated for their antiviral potential and found to inhibit filoviruses, flaviviruses or coronaviruses.

Mammal or human hosts infected with a filovirus, flavivirus or coronavirus can be treated by administering to said mammal or human an effective amount of an acyclic fleximer nucleoside analogue of the present invention and such compounds can be administered by any appropriate route, for example, orally, parenterally, intravenously, intradermally, subcutaneously, or topically, in liquid or solid form.

The present invention relates to a method for treating a filoviral, flaviviral or coronaviral infection, comprising the administration, to a patient, of an effective amount of at least one acyclic fleximer nucleoside analogue of the present invention and/or of a composition containing same. In general, the acyclic fleximer nucleoside analogues, as active agents, of this invention will be administered in a therapeutically effective amount by any of the accepted modes of administration for agents that serve similar utilities. The effective amount will be that amount of an acyclic fleximer nucleoside analogue of the present invention that would be understood by one skilled in the art to provide therapeutic benefits. The active agent can be administered once a week, twice or more times per week, once a day, or more than once a day. As indicated above, all of the factors to be considered in determining the effective amount will be well within the skill of the attending clinician or other health care professional.

For example, therapeutically effective amounts of an acyclic fleximer nucleoside analogue of the present invention may range from approximately 0.05 to 50 mg per kilogram body weight of the subject per day; preferably about 0.1-25 mg/kg/day, more preferably from about 0.5 to 10 mg/kg/day. Thus, for administration to a 70 kg person, the dosage range would most preferably be about 35-700 mg per day.

In general, an acyclic fleximer nucleoside analogue of the present invention can be administered as pharmaceutical compositions by any one of the following routes: oral, systemic (e.g., transdermal, intranasal or by suppository), or parenteral (e.g., intramuscular, intravenous or subcutaneous) administration. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration and bioavailability of the acyclic fleximer nucleoside analogue. For delivery via inhalation the compound can be formulated as liquid solution, suspensions, aerosol propellants or dry powder and loaded into a suitable dispenser for administration.

A composition comprising an acyclic fleximer nucleoside analogue of the present invention may be combined with at least one pharmaceutically acceptable carrier, excipient or diluent. Some examples of acceptable excipients are those that are non-toxic, will aid administration, and do not adversely affect the therapeutic benefit of the compound of the invention. Such excipient may be any solid, liquid, semi-solid or, in the case of an aerosol composition, gaseous excipient that is generally available to one of skill in the art.

Solid pharmaceutical excipients useful in the invention may include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable pharmaceutical excipients and their formulations are described in Remington's Pharmaceutical Sciences, edited by E. W. Martin (Mack Publishing Company, 18th ed., 1990). The amount of an acyclic fleximer nucleoside analogue of the present invention can vary within the full range employed by those skilled in the art. For example, a composition may contain, on a weight percent (wt %) basis, from about 0.01-99.99 wt % of an acyclic fleximer nucleoside analogue of the present invention based on the total formulation, with the balance being one or more suitable pharmaceutical excipients.

The pharmaceutical composition according to the invention preferably comprises an amount of an acyclic fleximer nucleoside analogue of the present invention of between 5 µg and 1000 mg, preferably between 1 and 500 mg, preferably between 5 and 100 mg. The ratio between the amounts by weight of an acyclic fleximer nucleoside analogue of the present invention and of pharmaceutically acceptable carrier is between 5/95 and 95/5, preferably between 20/80 and 80/20.

The acyclic fleximer nucleoside analogues of the present invention may be the only active ingredients, or they may be combined with other active ingredients. The pharmaceutical composition according to the invention may thus also comprise at least one other pharmaceutical active agent, in particular at least one other medicament used for the treatment of viral infection. In particular, the composition according to the invention may also comprise, or be combined with, one or more other antivirals. Generally, any antiretroviral may be combined, namely nucleoside or nucleotide and non-nucleoside inhibitors, protease inhibitors, entry inhibitors, etc.

The acyclic fleximer nucleoside analogues of the present invention or compositions comprising same -continued 1, R = H, from 5
2, R = Ac, from 6

Reagents and conditions:
(a) Na$_2$SO$_3$, 30% EtOH, 120° C., 84%;
(b) Ac$_2$O, NEt$_3$, DMAP, 97%;
(c) Pd$_2$dba$_3$•CHCl$_3$, 5 or 6, CuI, CsF, DMF, 50° C., 20%.

Treatment with sodium sulfite in a 30% ethanol/water solution resulted in simultaneous deacetylation and selective deiodination to provide key intermediate 5. Acetylation of 5 then generated 6, the 5' protected intermediate needed for the prodrug synthesis. In parallel, the organometallic coupling reagent 7 was synthesized starting from the commercially available 2-amino-4-methoxypyrimidine.(27,28) Stille coupling of 7 to 5 gave 1. Alternatively, using the acetylated 6, Stille coupling provided the desired double prodrug 2.

Synthesis of the McGuigan ProTide (29-33) started with commercially available L-alanine and utilized literature procedures to generate the phosphoramidate 8 (Scheme 2).(34) Reaction of 8 with fleximer 1 in the presence of tert-butyl magnesium chloride then provided the desired McGuigan ProTide 3 in 69% yield.

Scheme 2.

1 +

8

3

(a) tBuMgCl, THF, 69%.

After the successful synthesis of the three Flex-analogues 1, 2, and 3, the compounds were screened against a panel of filoviruses including EBOV, MARV, and SUDV, as well as other hemorrhagic fever viruses such as Lassa and Rift Valley Fever. The first series of assays utilized HeLa cells infected with live-virus isolates of EBOV (Makona), SUDV (Gulu), and MARV (Ci67). Activity against all three viruses was observed for the McGuigan prodrug 3, with the best activity against SUDV (Table 1).

The second series of assays utilized Huh7 cells infected with recombinant reporter EBOV, Lassa, and Rift Valley Fever viruses. As observed in the first series of assays, compound 3 was active against EBOV at a similar concentration, however, compound 1 exhibited the best activity (EC$_{50}$=2.2±0.3 lM) against EBOV in Huh7 cells (Table 2).

TABLE 1

Antiviral activity of nucleoside analogues in infected HeLa cells, values are in 1M.

| CMPD | EBOV | | SUDV | | MARV | |
| --- | --- | --- | --- | --- | --- | --- |
| | EC$_{50}$ | CC$_{50}$ | EC$_{50}$ | CC$_{50}$ | EC$_{50}$ | CC$_{50}$ |
| 1 | >100 | >100 | >100 | >100 | >100 | >100 |
| 2 | 44 ± 13 | >100 | 20 ± 10 | >100 | 70 ± 27 | >100 |
| 3 | 29 ± 9 | >100 | 7 ± 2 | >100 | 62 ± 13 | >100 |

EC$_{50}$: Effective concentration showing 50% inhibition of virus-induced Cytopathic effect CPE
CC$_{50}$: Cytotoxic concentration showing 50% inhibition of cell survival

TABLE 2

Antiviral activity of nucleoside analogues against recombinant reporter viruses in Huh7 cells in 1M.

| CMPD | EBOV | | Lassa Virus | | Rift Valley Fever | |
| --- | --- | --- | --- | --- | --- | --- |
| | EC$_{50}$ | CC$_{50}$ | EC$_{50}$ | CC$_{50}$ | EC$_{50}$ | CC$_{50}$ |
| 1 | 2.2 ± 0.3 | >50 | >50 | >50 | >50 | >50 |
| 3 | 27.2 ± 2.2 | >50 | >50 | >50 | >50 | >50 |

EC$_{50}$: Effective concentration showing 50% inhibition of virus-induced Cytopathic effect CPE
CC$_{50}$: Cytotoxic concentration showing 50% inhibition of cell survival Infectious diseases such as EBOV continue to pose a serious health threat due to the high mortality rates associated with these deadly viruses. While ongoing studies have identified various therapeutics as potential EBOV treatments, there are limited vaccines or therapeutics available, and as such, it is imperative that an effective treatment option is developed. Within this study it was found that both compounds 1 and 3 exhibited antiviral activity against a recombinant reporter EBOV in Huh7 cells, though surprisingly the McGuigan prodrug was ~10-fold less potent (EC$_{50}$=2.2±0.3 lM and 27.2±2.2 lM respectively). Against wild-type viruses in HeLa cells, compound 1 had no detectable activity, though compound 3 inhibited both EBOV and SUDV (EC$_{50}$=29±9 and 7±2 lM respectively). The difference in activity of 1 in the Huh7 cells compared to the HeLa cells is most likely due to a difference in specific metabolism of the compound in those cells lines.

Three compounds in Table 3 were tested in Ebola/Makona (except Hp083), Ebola/Sudan and Marburg infection assay with HeLa, and HFF cell lines. Stock solutions were made at 10 mM in 100% DMSO. Compounds were dispensed 2 h before infection by HP D300 directly from the 100% DMSO stock into assay wells with cells. DMSO was normalized in all wells to final 1%. Compound activity was tested in a 8-point dose response with 3 fold step dilution (see table below). The titration started at 100 μM (final) and repeated 3 times on a single plate (n=3).

TABLE 3

| | 1 | 2 | 3 | 4 | 5 | 6 | 7 | 8 |
|---|---|---|---|---|---|---|---|---|
| HP105 | 100 | 33.33 | 11.11 | 3.70 | 1.23 | 0.41 | 0.14 | 0.05 |
| MR064 | 100 | 33.33 | 11.11 | 3.70 | 1.23 | 0.41 | 0.14 | 0.05 |
| HP083 | 100 | 33.33 | 11.11 | 3.70 | 1.23 | 0.41 | 0.14 | 0.05 |

16 wells were treated with 1% DMSO to be used as a neutral control. Additionally, 16 wells were not infected and were used as a low signal controls. Cells were infected with EBOV(Makon) in Hela with Multiplicity Of Infection (MOI)=1.5, Marburg (Ci-67) MOI=1.0 and Sudan (Gulu) MOI=0.1. Infection was stopped after 48 h by fixing cells with a formalin solution.

To detect infected cells an immuno-staining was completed with anti-GP antibodies. Images were acquired by the PE Opera confocal platform using a 10× objective and were analyzed using Acapella software. Signal for GP-staining was converted into % infection. The number of nuclei per well was used to determine % viability of cells (in comparison to infected but untreated controls). Data was analyzed using GeneData software. % of infection was converted into % Inhibition (% INH) for each well using plate controls.

FIG. 2 shows the plates statistics for the three different viruses indicating the level of infection and number of nuclei. Also included are three graphs showing the use of a control compound E864 on the three different viruses.

FIGS. 3, 4 and 5 show that one of the tested nucleosides, that being nucleoside 3, demonstrated highest antiviral activity in Hela cells against EBOV ($EC_{50}$ 29.10), SUDV ($EC_{50}$ 6.85) and MARV ($EC_{50}$ 62.29).

A number of flaviviruses cause human disease, particularly hemorrhagic fevers and encephalitis. Each species of flavivirus has a unique geographic distribution; however, taken together, flaviviruses, and flavivirus-induced disease, can be found world-wide. One of the more commonly known diseases is dengue fever, or dengue hemorrhagic fever/shock, which was first described as a virus-induced illness in 1960. Dengue fever occurs in tropical and temperate climates—and is spread by Aedes mosquitoes. The symptoms include febrile headache, joint pain, rash, capillary leakage, hemorrhage and shock. Another common flavivirus-induced disease is yellow fever. Yellow fever is found in tropical Africa and America and is transmitted by mosquitoes. The mortality rate is approximately 30% and symptoms include febrile headache, myalgia (muscle pain), vomiting and jaundice. Examples of some of the other diseases caused by flavivirus species include Japanese encephalitis, and West Nile fever. These diseases share many of the same symptoms, which may include headache, myalgia, fever, hemorrhage, encephalitis, paralysis and rash.

Dengue virus (DV) is a mosquito-borne pathogen that causes dengue fever (DF) and severe life threatening illness, dengue hemorrhagic fever/dengue shock syndrome (DHF/DSS). DV is a small, enveloped, positive-stranded RNA virus that belongs to the Flavivirus genus of the Flaviviridae family which also includes Zika virus, and yellow fever virus. Zika virus (ZIKV) is an arthropod-borne Flavivirus and since 2015 has rapidly spread through South and Central America and the Caribbean. ZIKV was first discovered in Uganda in 1947 in the course of mosquito and primate surveillance. The infection, known as Zika fever, often causes no or only mild symptoms, and had until now remained a rare disorder confined within a narrow equatorial belt from Africa to Asia. The World Health Organization (WHO) has declared the Zika virus an international public health emergency, prompted by growing concern that an increased incidence of microcephaly in fetuses born to mothers infected with ZIKV is linked to the recent outbreaks.

Additional testing was conducted on multiple types of viruses using compounds 2MR04, MR064, HP105 and HP083 and sinefungin as an inhibitory positive control. The compounds were solubilized in water (1 mM) with a final concentration of 50 μM. The following enzymes were used (independent triplicates, except for DV experiment performed induplicate):

1) SARS-CoV nsp14 (N7 MTase): 10 nM
2) MERS-CoV nsp14 (N7 MTase): 125 nM
3) MERS-CoV nsp10/nsp16 (2'O MTase): 500 nM
4) Zika virus NS5 MTase: 500 nM
5) Dengue virus NS5 MTase: 500 nM
6) hPMV CRIV+: 1 μM
7) human N7 MTase (hN7 or RNMT): 20 nM Methyltransferase (MTase) is involved in RNA capping process and important for mRNA stability, protein synthesis and also virus replication, thus MTase is an attractive target in designing MTase inhibitors. Sinefungin, a well-known anti-fungal AdoMet analogue and which is known to inhibit methylation and viral replication in other flaviviruses, thus, making MTase a valid target anti-virus drug discovery The results are shown in FIG. 6 for severe acute respiratory syndrome (SARS), Middle East respiratory syndrome (MERS), ZIKA, Dengue, hMPV (Human metapneumovirus), and RNMT (RNA Guanine-7 Methyltransferase). As can be seen, 2MR04 inhibits several MTase (SARS-nsp14, Dengue & Zika virus MTases as well as hMPV MTase) in contrast to the RNMT (RNA Guanine-7 Methyltransferase), which is not inhibited. In addition, it was observed that MR064 and HP-105 also inhibited Dengue virus NS5 MTase.

Additional testing was conducted at 50 μM on other mononegavirus MTases (in triplicate):

1) human N7 MTase (hN7 or RNMT): 20 nM
2) hMPV MTase: 1 μM
3) RSV MTase: 4 μM
4) SUDV MTase: 4 μM FIG. 7 shows that compound 2MR04 was effective in strongly inhibiting the MTase activity of hMPV and RSV (Respiratory syncytial virus), viruses belonging to the family Pneumoviridae. The $IC_{50}$ values for 2MR04 was determined and shown in FIG. 8 wherein the $IC_{50}$ for the hN7 MTase was about 49 μM, about 31 μM on hMPV, and about 18 μM for RSV.

FIGS. 9 and 10 show the results for determining the $IC_{50}$ for the Zika NS5-MTase and DV NS5-MTase using three compounds, that being, MR064, HP105 and 2MR04. It was found that 2MR04 strongly inhibits both the Zika NS5-MTase and DV NS5-MTase with an $IC_{50}$ of about 22 μM. Also in FIG. 15, it is shown in another testing that 2 MR04 inhibited even stronger, that being, with an IC50 of about 17 μM.

The fleximer 2MR04 was also tested for MERS and SARS-Cov. In vitro enzymatic assays were carried out in polymerase assay buffer (20 mM Hepes pH 7.5; 10 mM KCl; 10 mM DTT; 4 mM MgCl2) in case of MERS-Coronavirus and buffer (20 mM Tris pH 8; 10 mM KCl; 1 mM DTT; 2 mM $MgCl_2$) in case of SARS-Coronavirus. For the reaction, 1 μM of MERS polymerase complex (12HC/7HC8) or 0.6 μM of SARS polymerase complex (12HC/7HC8) were mixed with 0.5 μM of a radiolabeled primer annealed to a template substrate and assembled at 30° C. for 30 min.

The primer extension was started by the addition of either 50 μM of each potential inhibitor or 50 μM of each inhibitor plus 20 μM of a NTPs mix. After incubation at 30° C., aliquots of reactions were quenched at various time points by the addition of an equal volume of loading buffer (formamide with 10 mM EDTA). Reaction products were loaded onto 20% polyacrylamide/7M urea gels, visualized using a PhosphorImager (Fuji), and quantified using ImageQuant Software (Fuji).

Figure 11:
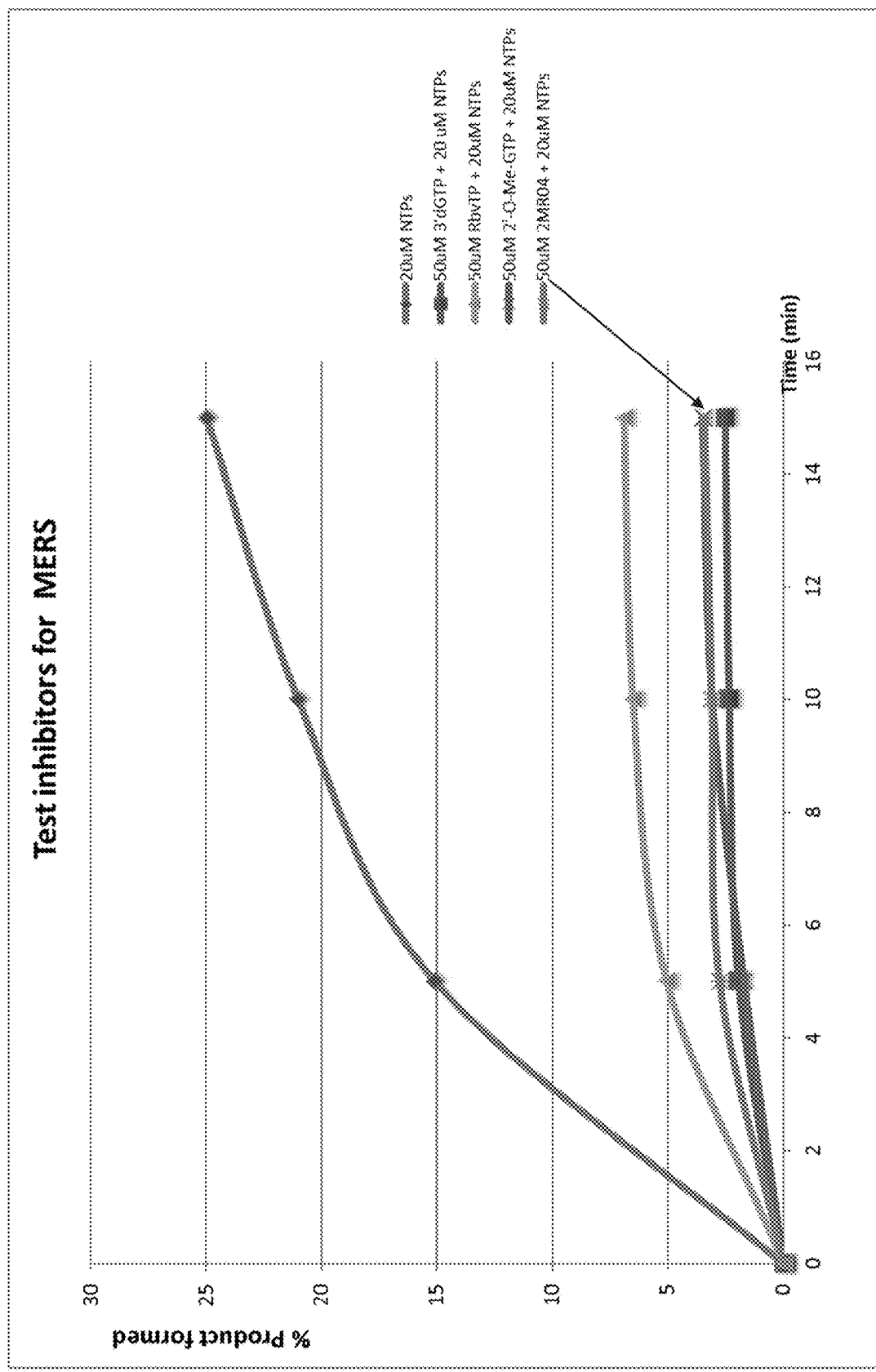
FIG. 11 shows test results using different viral inhibitors, compared to NTPs as a control, in the testing of MERS.
Figure 12:
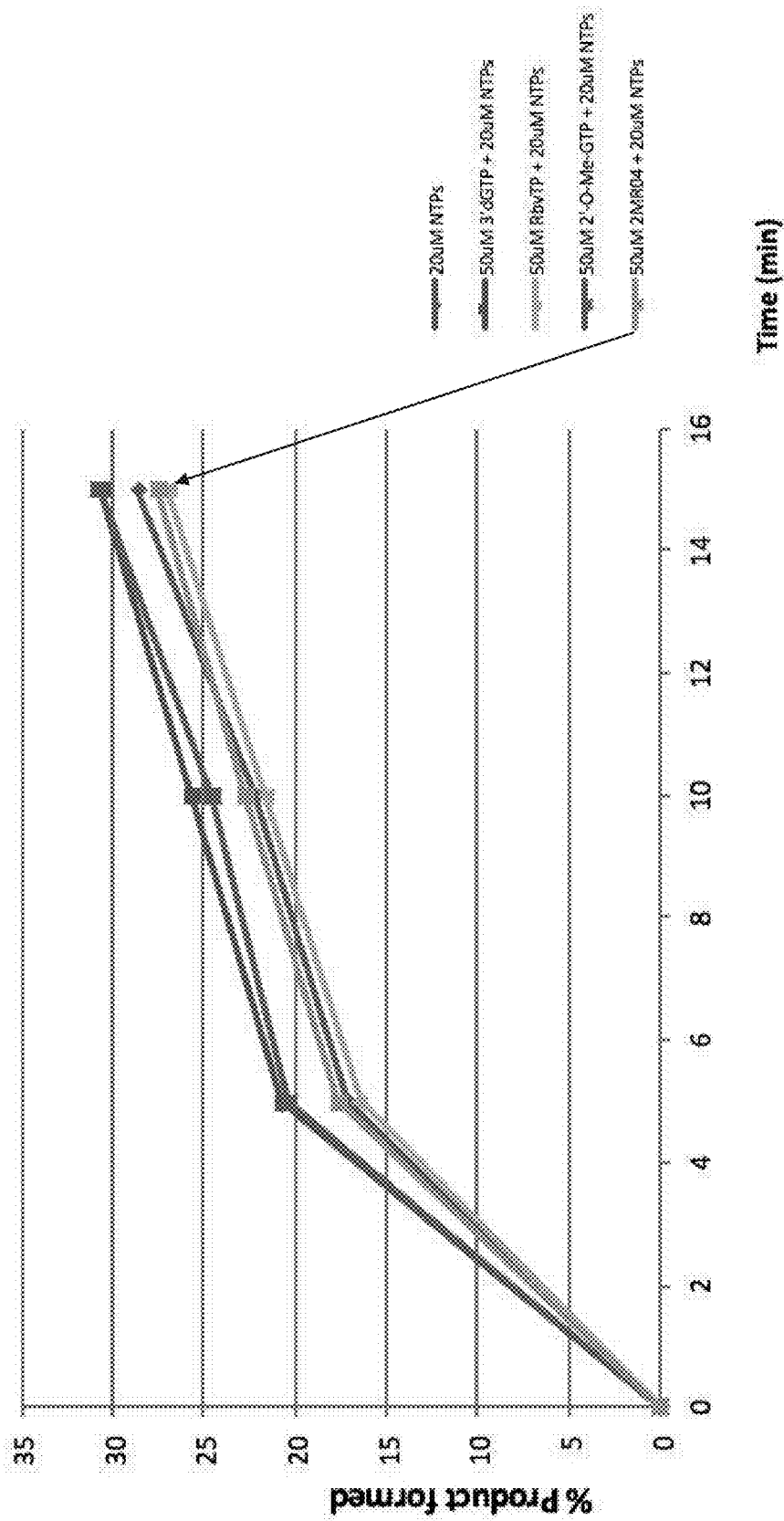
FIG. 12 shows test results using different viral inhibitors, compared to NTPs as a control, in the testing of SARS-CoV.

As noted in FIG. 11, the inhibitor 2MR04 is as effective as the 3'dGTP inhibitor (known as an N-pocket inhibitor) along with 2'-O-methyl GTP which is able to act as a chain terminator and inhibit RNA synthesis in the testing for MERS inhibitors. The percentage of product formed is greatly reduced relative to the control of 20 μM NTPs. In contrast. the results for the inhibitor 2MR04 were found to be comparable to the other inhibitors as shown in FIG. 12.

Figure 13:
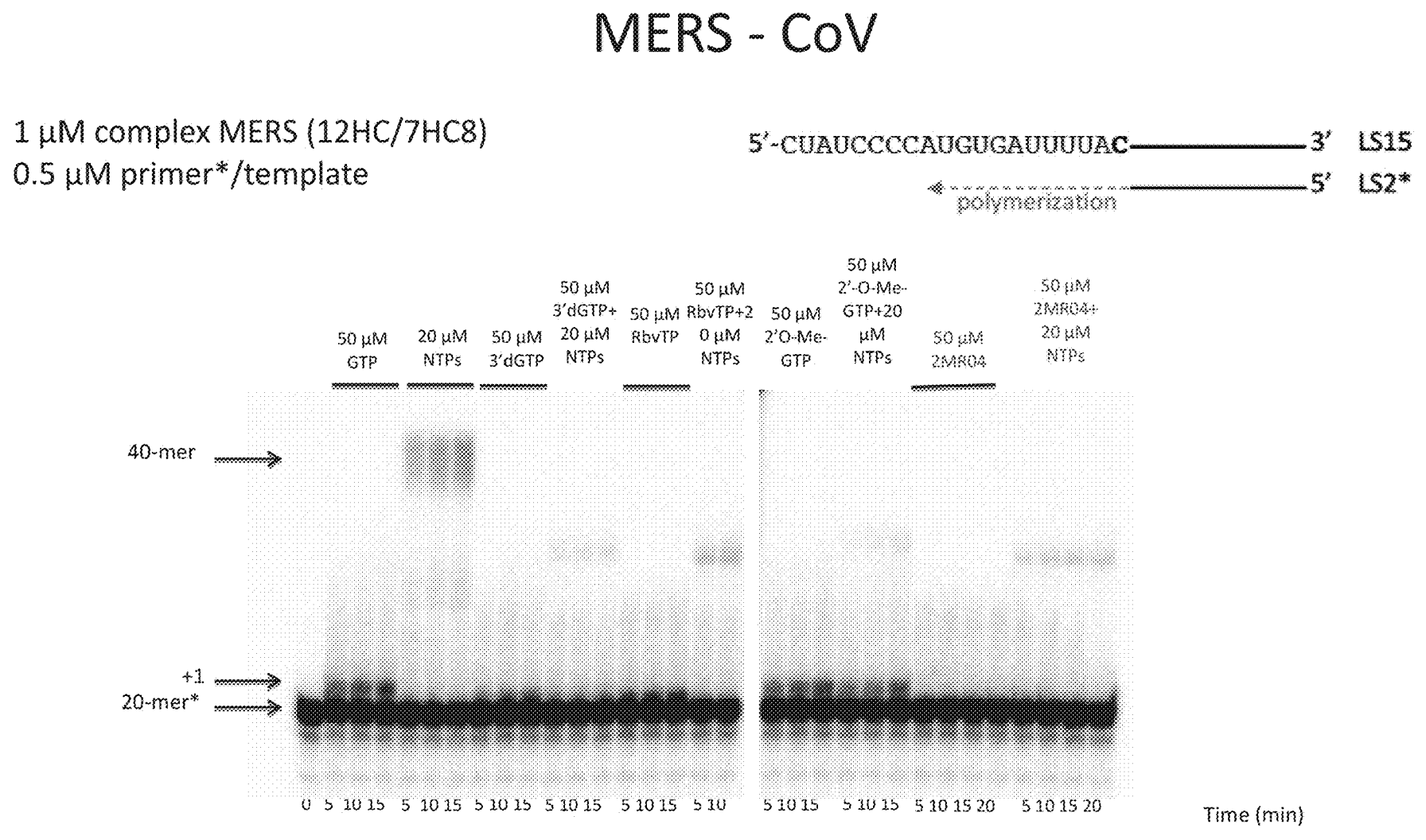

FIG. 13 shows blots of products formed using the MERS inhibitors and it is evident that the inhibitor 2MRO4 (alone or with NTPs) was as effective, not more effective, in reduction of oligonucleotide synthesis. Likewise FIG. 14 shows that using the SARS inhibitors that the inhibitor 2MRO4 (alone or with NTPs) was as effective in reduction of oligonucleotide synthesis.

REFERENCES

The contents of the references cited herein are incorporated by reference herein for all purposes.

1. Boisen M L, Hartnett J N, Goba A, et al. *Annu Rev Virol.* 2016; 3:147-171.
2. Moghadam S R J, Omidi N, Bayrami S, Moghadam S J, Seyed Alinaghi S. *Asian Pac J Trop Biomed.* 2015; 5:260-267.
3. Rougeron V, Feldmann H, Grard G, Becker S, Leroy E M. *J Clin Virol.* 2015; 64:111-119.
4. Mendoza E J, Qiu X, Kobinger G P. *Trends Mol Med.* 2016; 22:164-173.
5. Lau M S, Dalziel B D, Funk S, et al. *Proc Natl Acad Sci USA.* 2017; 114:2337-2342.
6. L. H. Sun, Disease 'superspreaders' accounted for nearly two-thirds of Ebola cases, study finds, www.washington-post.com/news/to-your-health/wp/2017/02/13/disease-superspreaders-accounted-for-nearly-two-thirds-of-ebolacases-study-finds/?utm_term=.555a3aacb28a, (accessed Mar. 20, 2017, 2017).
7. Mire C E, Geisbert T W, Feldmann H, Marzi A. *Expert Rev Vaccines.* 2016; 15:1421-1430.
8. Qiu X, Audet J, Wong G, et al. *Sci Transl Med.* 2012; 4. 138ra181.
9. Geisbert T W, Hensley L E, Jahrling P B, et al. *Lancet.* 2003; 362:1953-1958.
10. Geisbert T W, Lee A C, Robbins M, et al. *Lancet.* 2010; 375:1896-1905.
11. Picazo E, Giordanetto F. *Drug Discov Today.* 2015; 20:277-286.
12. De Clercq E. *Nat Rev Microbiol.* 2004; 2:704-720.
13. De Clercq E, Neyts *J. Handb Exp Pharmacol.* 2009; 53-84.
14. Huggins J W, Zhang Z X, Monath T P. *Antiviral Res.* 1991; 15.
15. Coulombe R A, Sharma R P, Huggins J W. *Eur J Drug Metab Pharmacokinet.* 1995; 20:197-202.
16. Warren T K, Wells J, Panchal R G, et al. *Nature.* 2014; 508:402-405.
17. Warren T K, Jordan R, Lo M K, et al. *Nature.* 2016; 531:381-385.
18. Lo M K, Jordan R, Arvey A, et al. *Sci Rep.* 2017; 7:43395.
19. Seley K L, Zhang L, Hagos A. *Org Lett.* 2001; 3:3209-3210.
20. Seley K L, Zhang L, Hagos A, Quirk S. *J Org Chem.* 2002; 67:3365-3373.
21. Seley K L, Quirk S, Salim S, Zhang L, Hagos A. *Bioorg Med Chem Lett.* 2003; 13:1985-1988.
22. Polak M, Seley K L, Plavec *J. JAm Chem Soc.* 2004; 126:8159-8166.
23. Quirk S, Seley K L. Biochemistry. 2005; 44:13172-13178.
24. Quirk S, Seley K L. Biochemistry. 2005; 44:10854-10863.
25. Seley K L, Salim S, Zhang L, O'Daniel P I. *J Org Chem.* 2005; 70:1612-1619.
26. Peters H L, Jochmans D, de Wilde A H, et al. *Bioorg Med Chem Lett.* 2015; 25:2923-2926.
27. Minakawa N, Kojima N, Hikishima S, et al. *J Am Chem Soc.* 2003; 125:9970-9982.
28. Wauchope O R, Velasquez M, Seley-Radtke K. *Synthesis* (Stuttg). 2012; 44:3496-3504.
29. Mehellou Y, Balzarini J, McGuigan C. *Chem Med Chem.* 2009; 4:1779-1791.
30. Pertusati F, Serpi M, McGuigan C. *Antivir Chem Chemother.* 2012; 22:181-203.
31. Madela K, McGuigan C. *Future Med Chem.* 2012; 4:625-650.
32. Cahard D, McGuigan C, Balzarini J. *Mini Rev Med Chem.* 2004; 4:371-381.
33. Pradere U, Garnier-Amblard E C, Coats S J, Amblard F, Schinazi R F. *Chem Rev.* 2014; 114:9154-9218.
34. Ross B S, Reddy P G, Zhang H R, Rachakonda S, Sofia M J. *J Org Chem.* 2011; 76:8311-8319.

That which is claimed is:

1. A fleximer nucleoside analogue selected from the group consisting of:

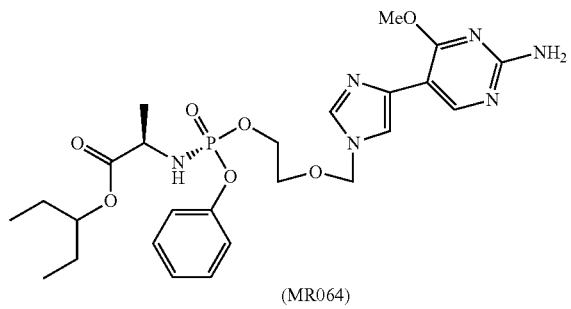

(MR064)

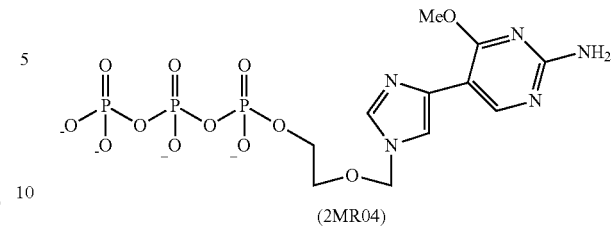

(2MR04)

and a pharmaceutically acceptable salt, isomer, hydrate, prodrug or solvate thereof.

2. The fleximer nucleoside analogue according to claim 1, having antiviral activity that inhibits or reduces the effects of a filovirus, flavivirus or coronavirus in a subject.

3. The fleximer nucleoside analogue according to claim 1, in a composition further comprising a pharmaceutically acceptable carrier.

4. The fleximer nucleoside analogue according to claim 1, in a composition further comprising an additional antiviral agent.

* * * * *

SEQUENCE LISTING

```
<160> NUMBER OF SEQ ID NOS: 1

<210> SEQ ID NO 1
<211> LENGTH: 20
<212> TYPE: RNA
<213> ORGANISM: Artificial Sequence
<220> FEATURE:
<223> OTHER INFORMATION: Synthetic construct

<400> SEQUENCE: 1
cuauccccau gugauuuuac                                        20
```